United States Patent [19]
Andreotti

[11] Patent Number: 5,916,802
[45] Date of Patent: Jun. 29, 1999

[54] DEVICE FOR MEASURING ATP

[75] Inventor: Peter E. Andreotti, Boca Raton, Fla.

[73] Assignee: Fritz Berthold, Pforzheim, Germany

[21] Appl. No.: 08/904,831

[22] Filed: Aug. 1, 1997

Related U.S. Application Data

[63] Continuation-in-part of application No. 08/801,019, Feb. 19, 1997, abandoned.

[51] Int. Cl.$^6$ ........................................... C12M 1/40
[52] U.S. Cl. ........................... 435/287.7; 435/287.9; 435/288.1; 435/306.1; 435/309.1
[58] Field of Search ................... 435/8, 30, 31, 435/287.4, 34, 287.7, 39, 287.9, 288.1, 288.3, 288.4, 288.7, 304.1, 305.1, 305.2, 306.1, 307.1, 309.1, 810; 422/58, 61; 600/572, 584

[56] References Cited

U.S. PATENT DOCUMENTS

| | | |
|---|---|---|
| 3,423,290 | 1/1969 | Seamans, Jr. . |
| 3,575,811 | 4/1971 | Chappelle et al. . |
| 3,933,592 | 1/1976 | Clendenning . |
| 4,014,745 | 3/1977 | Fletcher et al. . |
| 4,144,134 | 3/1979 | Plakas . |
| 4,234,681 | 11/1980 | Dluca-McElroy . |
| 4,985,631 | 1/1991 | Wannlund et al. . |
| 5,082,628 | 1/1992 | Andreotti et al. . |
| 5,159,197 | 10/1992 | Wannlund . |
| 5,258,285 | 11/1993 | Aegidius . |
| 5,278,075 | 1/1994 | Stone . |
| 5,366,867 | 11/1994 | Kawakami et al. . |
| 5,558,986 | 9/1996 | Lundin . |

FOREIGN PATENT DOCUMENTS

| | | |
|---|---|---|
| 126019 | 5/1984 | European Pat. Off. . |
| 0 309 429 | 3/1989 | European Pat. Off. . |
| 93/00994 | 1/1993 | WIPO . |
| 95/07457 | 3/1995 | WIPO . |
| 95/25948 | 9/1995 | WIPO . |

OTHER PUBLICATIONS

Schram, E, "Evolution of Bioluminescent ATP Assays," Vrije Universiteit Brussel, 1640–Sint–Genesius–Rode, *Bioluminescence and Chemiluminescence*, Belgium, pp. 407–412 (No date provided).

Ulrich, Peter G. et al., "Bioluminescence in the Microbiology Laboratory", *Amer. Clin. Prods. Rev.,* 1984.

Flickinger, Bruce, "Plant Sanitation Comes to Light," *Food Quality,* pp. 22–36, 1996.

Flickinger, Bruce, "Light Up Your Plant Part II: Into the Laboratory," *Food Quality,* pp. 20–33, 1997.

Flowers, Russ et al., An Evaluation of Five ATP Bioluminescence Systems, *Food Quality,* pp. 23–33. 1997.

*Primary Examiner*—William H. Beisner
*Attorney, Agent, or Firm*—Banner & Witcoff, Ltd.

[57] ABSTRACT

A method of taking a sample of an inoculated culture medium and measuring the amount of ATP using a luciferase/luciferin reaction. Additional samples are taken at later time intervals to determine whether anything is growing in the medium. Luciferase/luciferin reagent is immobilized on an absorbent tip of a sampling device in order to stabilize the luciferase/luciferin reagent and to provide a convenient means to combine the luciferase/luciferin reagent with the sample. A counting tube containing an extraction reagent is employed to extract intracellular ATP from the sample. Chlorhexadine diacetate (CDA) is the preferred extraction reagent.

10 Claims, 6 Drawing Sheets

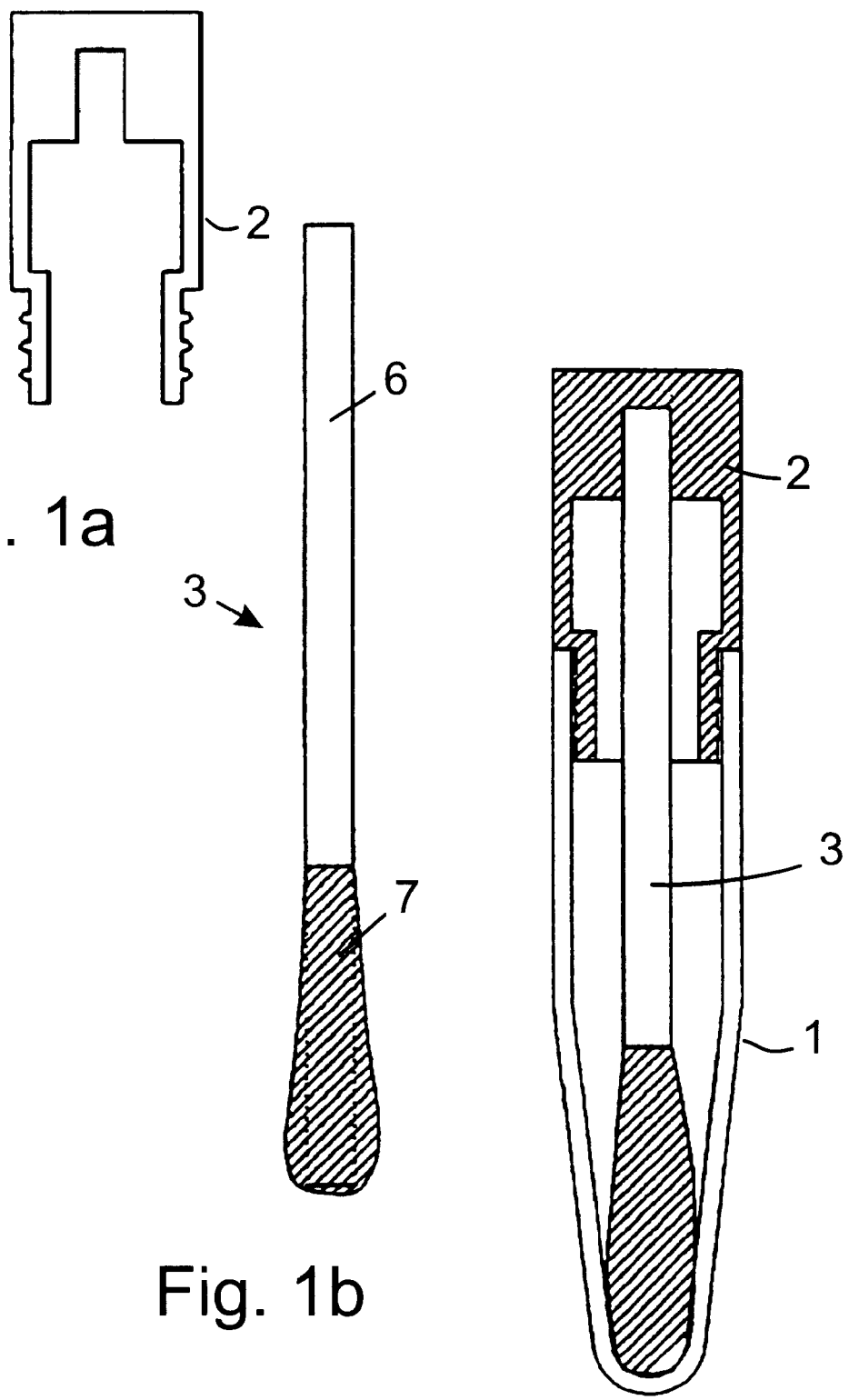

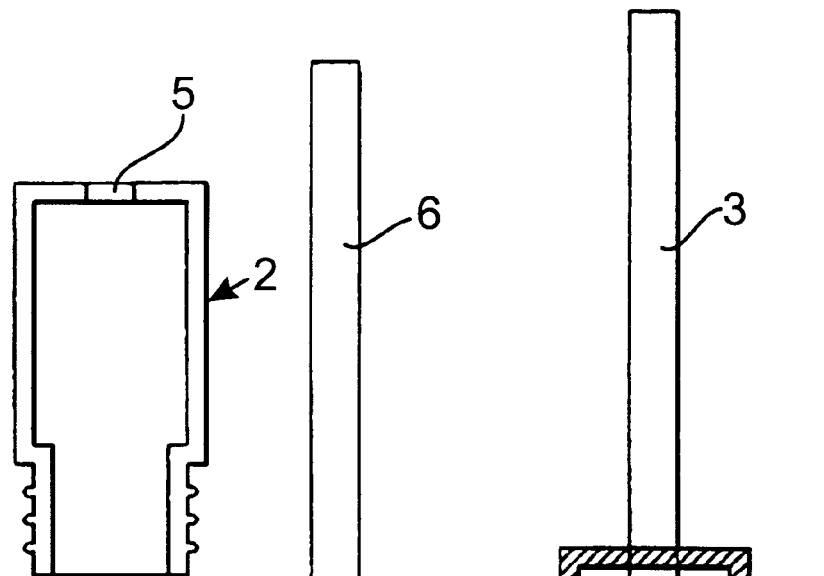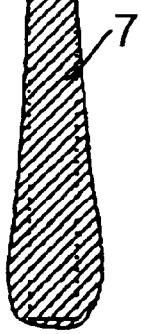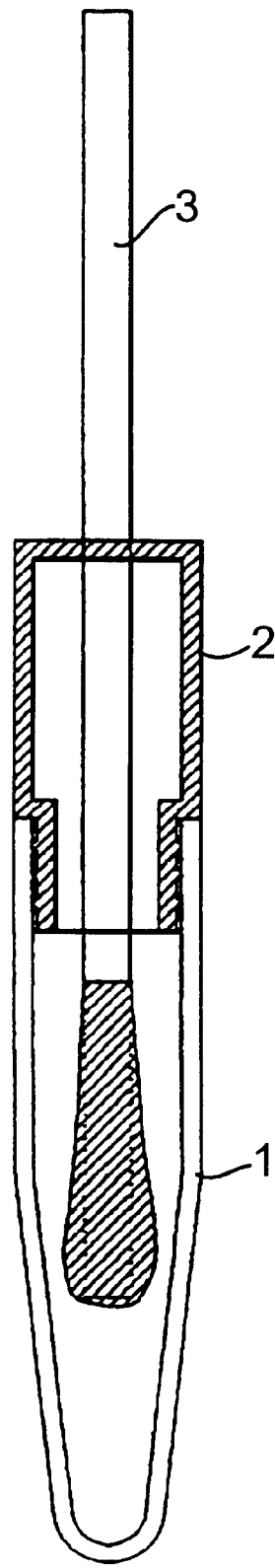
Fig. 2a
Fig. 2b
Fig. 2c

DEVICE FOR MEASURING ATP

This is a continuation-in-part of application Ser. No. 08/801,019, filed Feb. 19, 1997, now abandoned.

BACKGROUND OF INVENTION

This application relates to a sample measurement device and a method to detect extra cellular or intracellular ATP. The ATP is obtained from a culture medium or from a liquid, for example, a beverage, cosmetic, or pharmaceutical. The present invention measures growth of microorganisms, such as bacteria, yeast, mold, etc., using sequential measurements over time.

It is important in many industries, such as food preparation, medicine, beverages, toiletries, and pharmaceuticals, to provide clean and sanitary surfaces. In addition it is important to ensure that products are free of microorganisms such as bacteria which can contaminate and spoil the product. It is not enough to simply clean or sanitize a surface, or prepare a product under controlled sanitary conditions. Instead, a test must be performed to detect whether the surface or product is actually free of microorganisms. For instance, random areas of a surface, such as a food preparation surface, must be tested microorganisms to determine the general cleanliness of the surface. Or samples of the product itself must be tested to ensure that the product is not contaminated.

One of the oldest methods to check for presence of contaminants involves culturing samples for microorganisms. For example, a test surface is chosen and wiped with a swab, and then the swab is smeared onto a culture medium. Alternatively, a sample of the product itself, such as a beverage, cosmetic, or pharmaceutical, is placed in a culture medium. The medium is incubated and then checked for the presence of bacteria colonies grown in the medium. Over the years, various types of culture media have been developed along with numerous products based thereon. While the results of bacterial cultures are accurate, they are limited by the time it takes to incubate the culture, usually in the order of days.

In response for a need to obtain results more quickly, other methods for detecting microorganisms were developed. Research soon focused on the detection of biomass. Biomass includes living cells, dead cells, other biotic products such as blood, and food residue. It was discovered that biomass could be detected by detecting ATP, adenoisine triphosphate, a chemical found in all living organisms.

The specific test for ATP involves the "firefly" reaction. The following is the reaction:

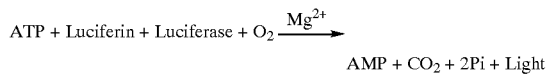

$$\text{ATP} + \text{Luciferin} + \text{Luciferase} + \text{O}_2 \xrightarrow{\text{Mg}^{2+}} \text{AMP} + \text{CO}_2 + 2\text{Pi} + \text{Light}$$

ATP, luciferin (D-luciferin cofactor), luciferase (enzyme) and oxygen are reacted in the presence of magnesium ion. Luciferin and luciferase are the same cofactor and enzyme present in fireflies that yields their namesake light. The products of the reaction are AMP (adenosine monophosphate), inorganic phosphate, carbon dioxide, and light (photons). The reaction, just as in fireflies, produces light. This light can be quantified and used to correlate to an amount of ATP. However, the amount of ATP does not necessarily relate directly to the number of microorganisms or bacterial cells or colonies. In addition ATP may be from non-microbe biomass such as beef blood whereby the amount of ATP would not be related to microorganisms.

The lack of correlation may be due to the variation in ATP concentration within cells and the degradation of ATP in dead cells. ATP is found in all living cells, but the amount of ATP in cells can vary significantly. For example, procaryotic cells have about one hundredth the amount of ATP as eukaryotic cells and different strains of bacteria will contain significantly different amount of ATP. In addition, if a cell is growing or about to divide, it will contain more ATP than a dormant cell. Furthermore, cells that have just died contain ATP and even dead cells may contain ATP. In dead cells, any ATP present may degrade, often caused by a reaction between ATP and intracellular enzymes contained within the dead cells. All of these variables in ATP concentration means that ATP testing is limited as a means to quantify the number of microorganisms or bacterial cells or colonies. However, ATP testing remains a method to qualitatively determine the presence of biomass including microorganisms.

Thus, the detection of ATP can be used to determine the presence of biomass, whether viable or nonviable. The ability to detect nonviable biomass is important, for instance, in testing a surface for cleanliness, because nonviable biomass (dead cells) such as food residue, can provide a medium for living cells to grow.

Typically, the luciferase, luciferin, and magnesium ion are sold as a single combined reagent, not as individual reagents. The luciferase must be at the proper pH of 7.8 in order to be effective, usually achieved by employment of a buffer solution. If the proper pH is not maintained, the reaction will not work efficiently, and the results will be erroneous. However, luciferase is unstable while in solution, and will degrade, particularly at higher temperatures. Generally, at room temperature, the luciferase solution will remain effective for a period of hours whereas at near freezing temperatures, the luciferase solution will last for a period of days. In addition, luciferin in solution is light sensitive. Light causes the dissolved luciferin to degrade. Once the luciferin has degraded, no cofactor remains to unleased the bioluminescent reaction resulting in false negatives.

To prevent degradation, the luciferin and luciferase can be dried and protected from light. Methods for drying include, but are not limited to, freeze drying and lyophilization. The luciferase is more stable if kept out of solution. When ready to use, the dried luciferin and luciferase are dissolved in, for example, water containing an appropriate buffer to form an aqueous solution having the proper pH.

By mixing the luciferase/luciferin reagent with a sample taken from a test surface, extracellular ATP is immediately reacted and detected. However, intracellular ATP cannot be detected unless the ATP is first extracted from within the cells. Typically, this is accomplished by mixing the sample with an extraction reagent (releasing reagent) which extracts the ATP from within the cells. The extracted ATP then can be mixed with the luciferase/luciferin reagent to produce the observable reaction. It is important that the extraction reagent chosen does not inactivate the luciferase/luciferin reagent.

The luciferase/luciferin reagent cannot be stored with the extraction reagent as it will inactivate the luciferase and/or the luciferin over time. It either is inactivated, no light will be produced when combined the ATP. Therefore, the luciferase/luciferin reagent and extraction reagent must be stored separately until the time the test is conducted.

The bioluminescent reaction of ATP and luciferase/luciferin has traditionally been conducted using two basic types of systems: vial systems and all-in-one swab devices. A vial system uses a series of vials containing the reagents necessary to conduct the ATP tests. An all-in-one swab device provides all of the reagents and the swab in a self-contained apparatus.

In a vial system, for example, a first vial contains the extraction reagent, a second vial contains dried luciferase/luciferin reagent, and a third vial contains a buffered solvent to rehydrate the luciferase/luciferin reagent. At the time of the test, the solvent is added to the vial containing luciferase/luciferin.

A sample is collected by wiping a prewetted swab across the testing surface. Typically, the swab is pre-wetted with saline. The swab containing the sample is placed in a test tube. Next, the proper amount of extraction reagent from the first vial is pipetted into the test tube containing the swab. After sufficient time has passed to ensure ATP extraction, the buffered solution containing hydrated luciferase/luciferin reagent is pipetted into the test tube and the luciferase is allowed to react with the ATP. The test tube is then placed into a luminometer where the amount of light produced by the reaction is measured. If more than one sample is taken, each sample is placed in its own test tube.

While vial systems produce correct results, there are deficiencies. One large problem is that the quantity of luciferase/luciferin solution prepared must be used within a short time period. If leftover solution is saved for later tests, the luciferase will degrade and ultimately become ineffective thus producing no reaction even in the presence of ATP. This problem is compounded by commercial producers of the luciferase/luciferin reagent that only sell the reagent in quantities that produce an amount of solution that is greater than that needed for individual tests. Furthermore, the dried enzyme is relatively costly. Thus the vial system results in waste of expensive reagents when only an individual test is required.

Another shortcoming of vial systems is that accurate pipetting and mixing of reagents is required. A pipette is used to transfer the reagents from vial to vial or vial to tube. While pipetting is accurate, it is laborious and time consuming. Further if any of the vials or pipettes are not sterile, any biomass contaminant will produce a false positive for the presence of ATP.

The all-in-one swab devices apply the same reaction as the vial systems but keep all of the reagents and swab in a self-contained apparatus that fits into a luminometer. All-in-one devices typically contain a swab that is placed in a plastic tube containing several chambers. An advantage to this system is that a unit dose of each reagent is provided for one test, thus avoiding waste of reagents when only one test is required. However, a certain procedure must be followed using an all-in-one device to ensure that the reagents are combined at the appropriate times.

In a typical all-in-one device, a swab pre-wetted with a wetting solution is placed in a sealed tube until ready for use. The wetting solution may contain an extractant. The sealed tube prevents evaporation of the wetting solution. At the appropriate time, the device is opened, the pre-wetted swab is removed, and a sample is collected by wiping the swab along the testing surface. If present, an extractant will extract intracellular ATP from the sample collected on the swab. The swab is then placed back in the tube and the tube is resealed and ready for ATP reaction with the luciferase/luciferin reagents.

Dried luciferase/luciferin reagents are kept in a dry, stable state in the tube until mixed with a buffer solution. The luciferase/luciferin may be kept isolated from the wet swab by placing the luciferase/luciferin in a separate chamber in the tube which can be broken to expose the luciferase/luciferin to the buffer solution. Alternatively, the luciferase/luciferin may be in the form of a pellet that can be placed in a sealed container or can be stuck to the bottom of the tube.

A sealed chamber at one end of the tube contains the buffer solution. The tube is squeezed to break the barrier wall between the chamber and portion of the tube containing the swab, resulting in release of the buffer solution. The tip of the tube is then shaken to allow the luciferase/luciferin regents to mix with the buffer solution, hydrate, and mix with the sample on the swab. The entire tube is then placed in a luminometer where the amount of light produced is measured.

While the all-in-one systems have overcome many of the problems of the vial systems, they have other shortcomings. For example, all-in-one systems are costly to manufacture since a complex tube arrangement is needed that is resealable and contains a breakable chamber to hold the buffer solution and possibly a second breakable chamber to hold the luciferase/luciferin.

Whatever system is used, the swabbing of the test surface should not itself contaminate the test surface. Thus, for example, the extracting agent used on the swab should not contain toxic chemicals that will leave toxic residues on the test surface.

Again, whatever system is used, the resulting tube containing the luciferase/luciferin and ATP is placed in a luminometer to read the light produced during the reaction. In the past, luminometers were designed with detectors aimed perpendicular to the axis of the sample tube so that when the sample is inserted in the luminometer's measurement chamber, the detector views the light produced by one side of the sample. Side-viewing detectors are appropriate if ATP is measured in solution. However, such detectors can be a problem in swab systems if the sample is located on only one side of the swab, and that side is placed on the opposite side of the detector, then the amount of light reaching the detector will be less. Thus, the quantitative light measurement becomes dependent upon how the sample is placed in the luminometer.

More recently, a luminometer with a bottom-reading detector was developed which avoids the problems of side-viewing luminometers. A bottom-reading luminometer views the bottom of the sample tube and provides an accurate reading independent of the orientation of the sample and whether the sample is in solution or absorbed onto a swab.

In co-pending application entitled Method and Apparatus For Rapid Hygiene Testing filed concurrently herewith, a method and device for bioluminescent ATP detection is described which provides a sampling device having an absorbent tip, such as a swab, wherein luciferase/luciferin reagent is immobilized in the tip. The luciferase/luciferin reagent is applied to the tip, or the tip is dipped into the reagent, and then the tip is dried by, for example, refrigerating at four degrees Celsius overnight, freeze drying, or lyophilization. The tip may be made out of a sterile fiber such as cotton or a synthetic fiber such as DACRON.

Several drops of a suitable wetting or extraction solution, such as chlorhexidine diacetate (CDA), water, or surfactants, are added to the test surface. The tip of the sampling device is wiped across the solution which activates the luciferase/luciferin reagent in the tip. The sampling device is then placed in a counting tube which in turn is inserted into a luminometer. By measuring the amount of light produced by the reaction, an amount of ATP can be determined. The sampling device containing a luciferase/luciferin enriched tip provides advantages over all-in-one systems since it is not as complicated nor as expensive.

Often it is desired to determine if and how quickly bacteria are growing. The all-in-one device or the sampling device above give a single reading and this they do not provide information as to whether the bacteria are growing.

It is the object of the present invention to provide sequential measurements of liquid culture samples to determine the presence and growth of bacteria through the detection and measurement of ATP over time. Another object is to use unit dose dried in the bottom of a counting tube and luciferase/luciferin dried in the swab tip. A further object is to use CDA dried in the bottom of a tube and luciferase/luciferin dried in the bottom of a counting tube. A further object of the present invention is to avoid waste of expensive reagents. Another object is to provide a system that uses a bottom-viewing detector and a non-light-absorbent tube that can be placed directly in the luminometer. Finally, an object of the present invention is to perform the test without the need to transfer reagents to a different container before being placed into the luminometer.

SUMMARY OF THE INVENTION

The present invention is directed to determining the presence and growth of bacteria or other microorganisms in a sample of culture medium or a sample obtained from a test surface by measuring ATP present in the samples. ATP is measured using a luciferase/luciferin reaction. Additional samples may be taken at later time intervals to determine whether anything is growing in the medium.

In one embodiment of the present invention, luciferase/luciferin reagent is immobilized on an absorbent tip of a sampling device. A sampling device contains a handle with an absorbent tip. In another embodiment, luciferase/luciferin is immobilized in a counting tube. This immobilization is important to stabilize the luciferase/luciferin reagent and to provide a convenient means to combine a unit dose of the luciferase/luciferin reagent with the sample. In addition, it was discovered that immobilized luciferase/luciferin reagent provides stable light emissions not obtainable with liquid luciferase/luciferin solutions.

In accordance with the present invention, a sample of a culture medium, or a sample obtained by swabbing a surface with a wet swab, is placed in a counting tube containing liquid or dried extraction reagent. Then a sampling device containing immobilized luciferase/luciferin is inserted in the tube. Luciferase reacts with any ATP present to produce light which is then measured by a luminometer.

In another embodiment, a sample of a culture medium, or a sample obtained by swabbing a surface with a wet swab, is placed in a counting tube containing dried extraction reagent. A sample of the culture/extraction reagent liquid is removed and placed in a counting tube containing dried (immobilized) luciferase luciferin. Such removal may be accomplished using a pipette or preferably with an untreated sampling device such as a swab. The swab is inserted into the tube and the sample is absorbed onto its tip. The tip is inserted into the bottom of a counting tube containing the dried luciferase/luciferin. Luciferase reacts with any ATP present to produce light which is then measured.

The present invention is also directed to the use of chlorhexidine diacetate (CDA) as an extraction reagent. CDA is a common ingredient in dental mouthwash. It was discovered that CDA provides excellent results when used with the dried luciferase/luciferin sampling device of the present invention. This was unexpected since CDA is known to quench the luciferase/luciferin reaction.

A preferred embodiment of the present invention uses a sampling means containing immobilized luciferase/luciferin reagent and a counting tube with dried CDA. Another preferred embodiment of the present invention uses an untreated sampling means, a tube containing dried CDA, and a counting tube containing immobilized luciferase/luciferin reagent.

These combinations provide a significant improvement over prior art methods that use the reagents in solution, or more expensive all-in-one systems that cannot be used for repeated measurements. After an initial 60–90 second reaction initiation period, light can be measured from the luciferase/ATP reaction for up to five minutes with consistent, even results. That is, using the dried luciferase/luciferin reagent and dried CDA, the emission of light over the five minute period is not time dependent as it is when using the same reagents in solution where the amount of light produced decreases over time.

BRIEF DESCRIPTION OF THE DRAWINGS

FIGS. 1a–1c depict side views of an embodiment of the present invention with a swab in a fixed position attached to the cap which is used to seal the tube containing dried CDA.

FIGS. 2a–2c depict side views of an embodiment of the present invention with a swab in a movable position with the handle which passes through the cap used to seal the tube containing the dried CDA.

DETAILED DESCRIPTION OF THE INVENTION

Figure 3:
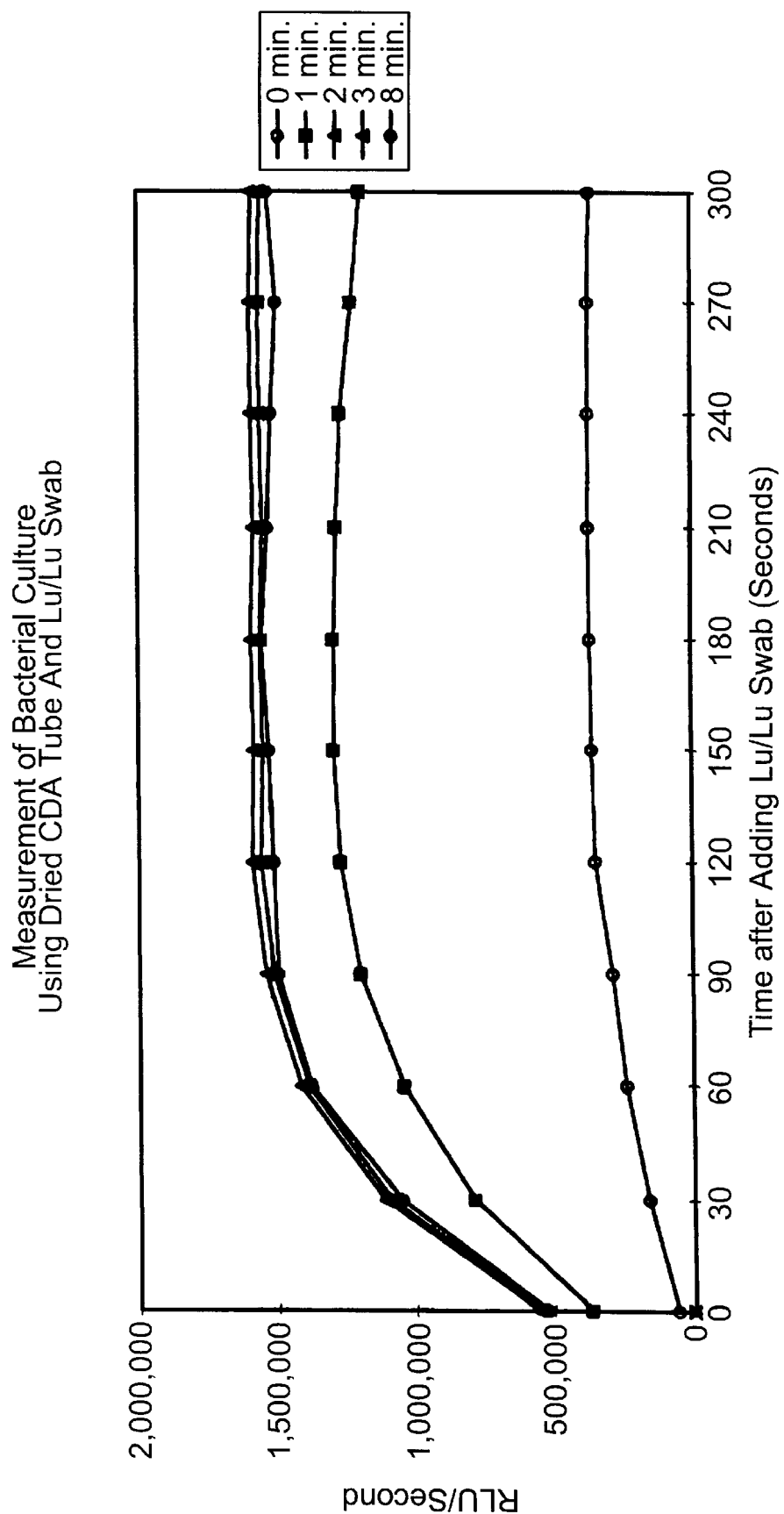
FIG. 3 depicts the measurement of ATP in a bacterial culture using dried CDA tube and a dried luciferase/luciferin swab.

The present invention may be used to test samples obtained from a variety of sources. Preferably samples for ATP measurement are obtained from culture mediums or from test surfaces, such as food preparation surfaces.

Any liquid or semi-solid culture medium and any suitable inoculation means may be used as within the skill of the art. For instance, the culture may be obtained by wiping a testing surface, such as a counter top, with a pre-wetter swab and then immersing the swab into the culture medium. Alternatively, the culture may be obtained by inoculation of the culture medium with a small portion of a liquid or solid product. The culture is then incubated and allowed to grow. Examples of products include beverages (e.g. beer, wine, or soda), water, pharmaceuticals, cosmetics, or toiletry products.

In accordance with the present invention, a sample is obtained from a culture medium. This sample may be obtained by any suitable means such as a pipette or an absorbent swab. Alternatively, a sample is obtained from a test surface by wiping the surface with a swab, for example.

The sample is placed in a counting tube containing a liquid or dried extraction reagent. A sampling device having a handle and an absorbent tip containing immobilized luciferase/luciferin reagent is inserted into the counting tube. The sampling device is rotated in the tube to ensure mixing.

If desired, the sampling device may also be used to remove the sample from the culture medium by dipping the absorbent tip into the medium prior to inserting the sampling device into the counting tube. Note that this method may contaminate the culture medium with the luciferase/luciferin reagent and should probably not be used if additional samples are going to be obtained from the culture medium.

The moisture of the sample rehydrates the luciferase/luciferin reagent and the extraction reagent (if dried) which allows the sample, extraction reagent, and luciferase/luciferin reagent to combine. The extraction reagent will extract intracellular ATP. The luciferase will react with any ATP (extracellular or intracellular) present in the sample to produce light. The quantity of light produced is measured by a luminometer.

In a preferred embodiment, a sample of a culture medium or from a test surface is obtained as described above. The sample is then inserted into a tube containing dried extraction reagent to extract ATP. This tube may be a counting-type tube or any other suitable tube. After extraction, the sample is removed from this tube by absorbing the sample onto the absorbent tip of an untreated sampling device. The tip is then inserted into a counting tube containing dried luciferase/luciferin. The sampling device is rotated to ensure mixing of the sample with the luciferase/luciferin. The counting tube, including the sampling device, is placed into a luminometer to measure light from the ATP-luciferase/luciferin reaction. Using an untreated sample device to remove a sample from the culture medium avoids contamination. Alternatively, a pipette may be used to remove a sample from the culture medium and/or to transfer the sample from one tube to another.

The counting tube may be a tube conventionally used for measuring light with a luminometer. The tube, also referred to as a vial, contains liquid or dried extraction reagent. It is important to use an extraction reagent in order to release intracellular ATP. Preferably the extraction reagent is dried, particularly when the sampling device containing the immobilized luciferase/luciferin is stored with the counting tube as a single package.

The dried extraction reagent must be a substance that, when hydrated, will extract ATP from within the microorganisms in the sample. Examples of extraction reagents include cationic and ionic detergents, and surfactants, such as the TRITON brand chemicals. The preferred extraction reagent is chlorhexidine diacetate (CDA). The amount of extraction reagent placed into each tube should calculated based on the specified volume of sample that will be added so that the extraction reagent will be dissolved to a concentration that is effective for the removal of ATP.

A tube coated with extraction reagent may be prepared by any suitable technique. For example, a concentrated extraction reagent solution is prepared and an appropriate amount is added to a counting tube. The solvent is removed leaving dried extraction reagent coating the bottom of the tube. Suitable methods to remove the solvent include placing the tube in a refrigerator at 4° C. overnight, lyophilization, and freeze drying. A concentrated solution is preferred to minimize the volume added and to shorten the time necessary to remove the solvent. The volume of concentrated extraction reagent solution can be determined by placing the amount of pure extraction reagent in the tube so that, later, when sample is added to it, the desired extraction reagent concentration is obtained. It is preferred that the extraction reagent be sterilized, for example using a microwave or autoclave.

The preferred extraction reagent is concentrated CDA solution, preferably having a concentration of 1 mg of pure CDA per 1 ml of water. CDA can be prepared in pH 7.8 Buffer containing HEPES (0.477 g/100 ml of water) without $Mg^{++}$.

12.5 to 25 $\mu$l of concentrated CDA solution is placed into the counting tube. The tube is placed, for example, in a refrigerator at 4° C. until the water is evaporated (about eight hours). Alternatively, the CDA solution may be freeze dried and lyophilized. The tube is left coated with dried CDA. This amount of CDA is designed to extract a culture sample volume of 125–250 $\mu$l. Preferably, the tubes contain 12.5 $\mu$l of dried 0.1% CDA and 200 $\mu$l culture samples are used. The sample is inserted into the tube containing the CDA and then 30–60 seconds is allowed to lapse to ensure that the CDA has extracted the ATP from the sample.

In order to obtain an accurate reading the counting tube should be made of a transparent material, at least transparent to the light waves produced by the reaction (yellow and green wavelengths). Examples of tube materials include glass, polystyrene, polypropylene, and polyethylene.

The tube lined with extraction reagent can be easily utilized in a unit dose format. The lined tubes can be kept in an airtight storage place by using a resealable lid on the container or the tubes can be packaged individually in disposable wrappers. Then, when needed, a tube can be taken out of storage, opened, and used one at a time. This allows a purchaser to buy the tubes in a large, cheap-per-unit quantity, yet use the tubes individually as needed over a long period to time.

The sampling device should be designed to fit in the counting tube. The sampling device contains a handle and a sterile absorbent tip containing immobilized luciferase/luciferin reagent. The absorbent tip may be used to collect a sample from a culture medium, if desired, and to insert it in the tube. The sampling device may be, but not limited to, a natural or synthetic fiber swab such as a cotton or DACRON swab, or a piece of absorbent paper or a sponge at the end of a handle.

The luciferase/luciferin reagent may be immobilized on the tip in any suitable manner such as by adding an excess amount of concentrated luciferase/luciferin reagent to the tip and then drying at 4° C. overnight, freeze drying, or lyophilizing.

In a preferred embodiment, 125 to 250 $\mu$l of a culture sample is removed and placed in a counting tube containing a dried extraction reagent using an untreated sampling device, pipette, spatula or any other suitable transfer means. The sample rehydrates the dried extraction reagent which in turn extracts any ATP from the sample. Then a sampling device containing immobilized luciferase/luciferin reagent is placed in the tube and the luciferase/luciferin reagent is rehydrated and released from the tip, by contact and mixing with the sample/extraction reagent combination. The tube is then placed into a luminometer which quantifies the amount of light produced by the reaction of ATP with luciferase.

A preferred embodiment of the present invention is shown in FIGS. 1a–1c. A dried extraction reagent coated tube 1, has a cap 2 that closes the tube, and a luciferin/luciferase enriched sampling device 3 having an absorbent end 7 and a handle 6 that is attached to the cap 2. The cap 2 is removable, reattachable, and resealable to the tube 1. The cap should form an airtight seal when attached to the tube 1 in order to protect the water-sensitive luciferin/luciferase in the sampling device and the dried extraction reagent in the tube. The sampling device should be combined with the cap so that the absorbent tip is in full contact with the bottom of the tube when the tube is completely sealed with the cap. Preferably the cap can turn in place in order to swirl the absorbent tip and mix the sample and reagents at the bottom of the tube.

Turning to FIGS. 2a–2c, the cap 2 preferably has a slot 5. The slot is slightly narrower than handle end 6 of the sampling device 3. The handle end 6 of the sampling device 3 is held in slot 5, but can be moved up and down and rotated. This embodiment allows the sampling device with the absorbent tip containing immobilized luciferase/luciferin reagent to be stored with the dried extraction reagent coated tube. The handle of the sampling device is simply pulled up so that the luciferase/luciferin reagent and the dried extraction reagent do not touch. In use, the cap and sampling device are removed, a culture sample is inserted into the tube, the cap and sampling device are replaced and the handle of the sampling means is pushed down and up and swirled in order to mix the reagents and the sample at the bottom of the tube.

The placement of the sampling device in the cap provides a dry, sterile environment until used and allows the sampling device to be held in a stable position or locked in place when the counting tube is placed in the luminometer. Otherwise, the sampling device may lean against the side of the tube or move around which could introduce error. The present configuration provides accurate and reproducible measurements.

Ideally, the radius of the tip of the sampling device and the radius of the inside of the tube should be close, e.g. about 4.0 mm each, to ensure intimate coupling of the tip, reagents, and tube.

The counting tube/sampling device of the present invention may be used by removing cap 2 to open tube 1. By removing cap 2, sampling device 3 is also removed. A sample of a bacteria culture is then added to the tube 1. The sample dissolves the dried extractant reagent which begins to extract ATP from the sample. Third, the cap 2 is reattached to tube 1 and the handle of sampling device 3 is pushed to immerse the absorbent tip 7 into the culture sample at the bottom 4 of the tube 1. The dried luciferin/luciferase reagent contained within the absorbent tip is rehydrated. Handle 6 is rotated to mix reagents and sample in bottom of tube. The counting tube is then placed into a luminometer. The amount of light produced by the reaction of ATP and luciferase is measured.

An extraction reagent lined tube and a luciferin/luciferase reagent enriched sampling device is easy to use. All of the reagents are present and the user need only add a sample to the tube by any means. Only a small volume of luciferase/luciferin reagent is required in the tip of the sampling device, but achieves more sensitivity for ATP than prior art methods.

Any suitable method may be used to prepare the luciferin/luciferase reagent for use on the absorbent tip of the sampling device of the present invention. In a preferred method, a stock luciferase solution is prepared by diluting luciferase to a concentration of 0.04 mg/ml in HEPES buffer pH 7.8 containing 4.766 g/liter HEPES, 1.22 g/liter magnesium sulfate, 0.744 g/liter EDTA, and 05% BSA. The stock luciferase solution is mixed with an equal volume of stock luciferin solution containing 2.0 mg/ml of D-luciferin dissolved in HEPES buffer pH 7 to 8, preferably pH 7.8. A volume of 10–20 $\mu$l (preferably 15 $\mu$l) of the luciferase/luciferin working solution is added and then dried in the absorbent tip of the sampling device or it is dried in the bottom of counting tubes. Alternatively, the concentrated working solution is diluted ten-fold in HEPES buffer and then approximately 125–175 $\mu$l (preferably 150 $\mu$l) of the diluted working solution is dried in the absorbent tip of the sampling device by dipping the tip in the diluted working solution and then drying it, or approximately 125–175 $\mu$l (preferably 150 $\mu$l) of the diluted working solution is dried in the bottom of counting tubes.

In another method, D-luciferin is dissolved in a sterile, pH 7.8, HEPES (N-2-hydroxyethylpiperazine-N-2-ethanesulfonic acid) buffer at 0.73 mg/ml. Luciferase is dissolved in sterile 0.5M Tris-succinate buffer pH 7.5 with 1% BSA (bovine serum albumin) to create a solution with a concentration of 1.0 mg/ml. Then 102.5 ml of D-luciferin solution, 23.75 ml of luciferase solution, and 41.25 ml of 3% BSA dissolved in water are combined to form the luciferase/luciferin solution. HEPES has a $pK_a$ of 7.55 at 20° C. and meets Good's criteria for a zwitterionic buffer.

Alternatively, the luciferase/luciferin reagent is reacted with the nylon tip of a sampling device to provide a covalent bond. Covalently bonded luciferase/luciferin remains active but remain connected to the nylon and not wipe off on the testing surface once the swabbing is finished.

EXAMPLES

Example 1

Bacterial cultures were prepared by inoculating *E. coli* in a nutrient broth culture medium. Counting tubes were coated with 25 $\mu$l of dried CDA. 0.2 ml samples of the bacterial culture were added to each of 5 CDA coated tubes to extract the bacterial ATP. Next a luciferase/luciferin coated DACRON tipped swab was added to each tube at a certain time after the addition of the bacterial culture as follows:

| Tube | Time (min) |
|------|------------|
| 1 | 0 |
| 2 | 1 |
| 3 | 2 |
| 4 | 3 |
| 5 | 8 |

Each tube was measured for 5 seconds in a luminometer immediately and at 30 second intervals after adding the luciferase/luciferin swab to the tube. The results are depicted in FIG. 3. The figure demonstrates that the extracted bacterial ATP was stable for up to 8 minutes after adding the sample to the tube. The figure also shows that the sample must be extracted at least one minute to obtain maximum light production, and the RLU output is stable for up to 5 minutes after an initial increase during the first 60–90 seconds after the luciferase/luciferin is added to the tube.

Example 2

Bacterial cultures were prepared by inoculating *E. coli* in a nutrient broth culture medium. A counting tube was coated with 25 $\mu$l of dried CDA. A 200 $\mu$l sample of the bacterial culture was added to the CDA coated tube to extract the bacterial ATP. After 60 seconds, a luciferase/luciferin coated DACRON tipped swab was added to the tube. Then, the light output from the tube was measured for 5 seconds in a luminometer immediately and at 30 second intervals for 300 seconds.

A 200 μl sample of the same bacterial culture was added to a tube containing 25 μl of liquid CDA to extract the bacterial ATP. After 60 seconds, 150 μl of luciferase/luciferin reagent was added to the tube. Then, the light output from the tube was measured for 5 seconds in a luminometer immediately and at 30 second intervals for 300 seconds.

Figure 4:
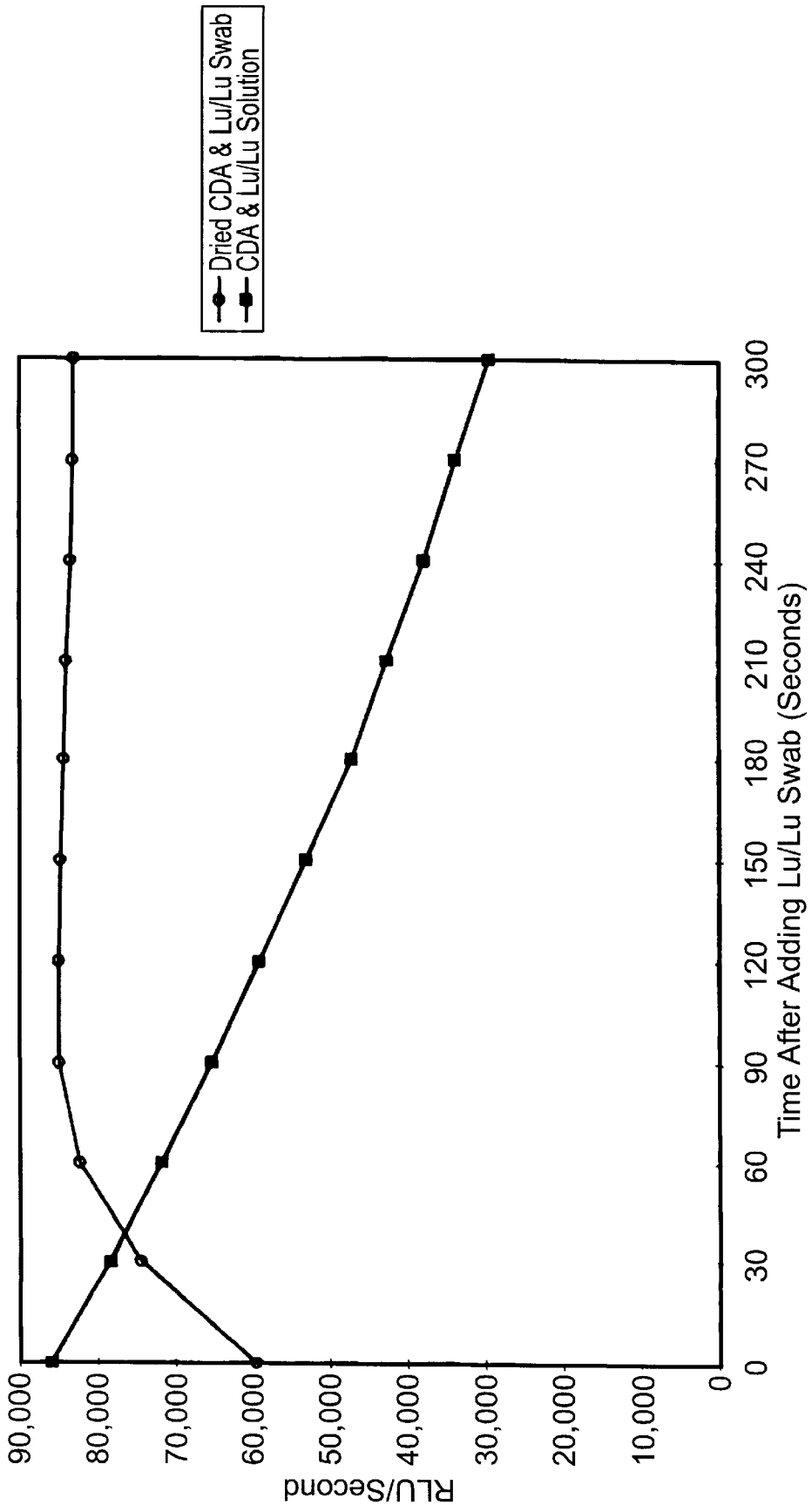
FIG. 4 depicts kinetics of bacterial culture measurement using dried CDA tube and dried luciferase/luciferin swab compared with CDA and luciferase/luciferin reagents in solution.

The results are shown in FIG. 4. As expected, the RLU output with the reagents in solution decreased over time. In contrast, the RLU output with the dried CDA and luciferase/luciferin swab increased over the initial 60–90 seconds until it reached a plateau level and stayed stable for at least 5 minutes thus the amount of light produced was not dependent on time after the initial 60–90 seconds.

Example 3

Figure 5:
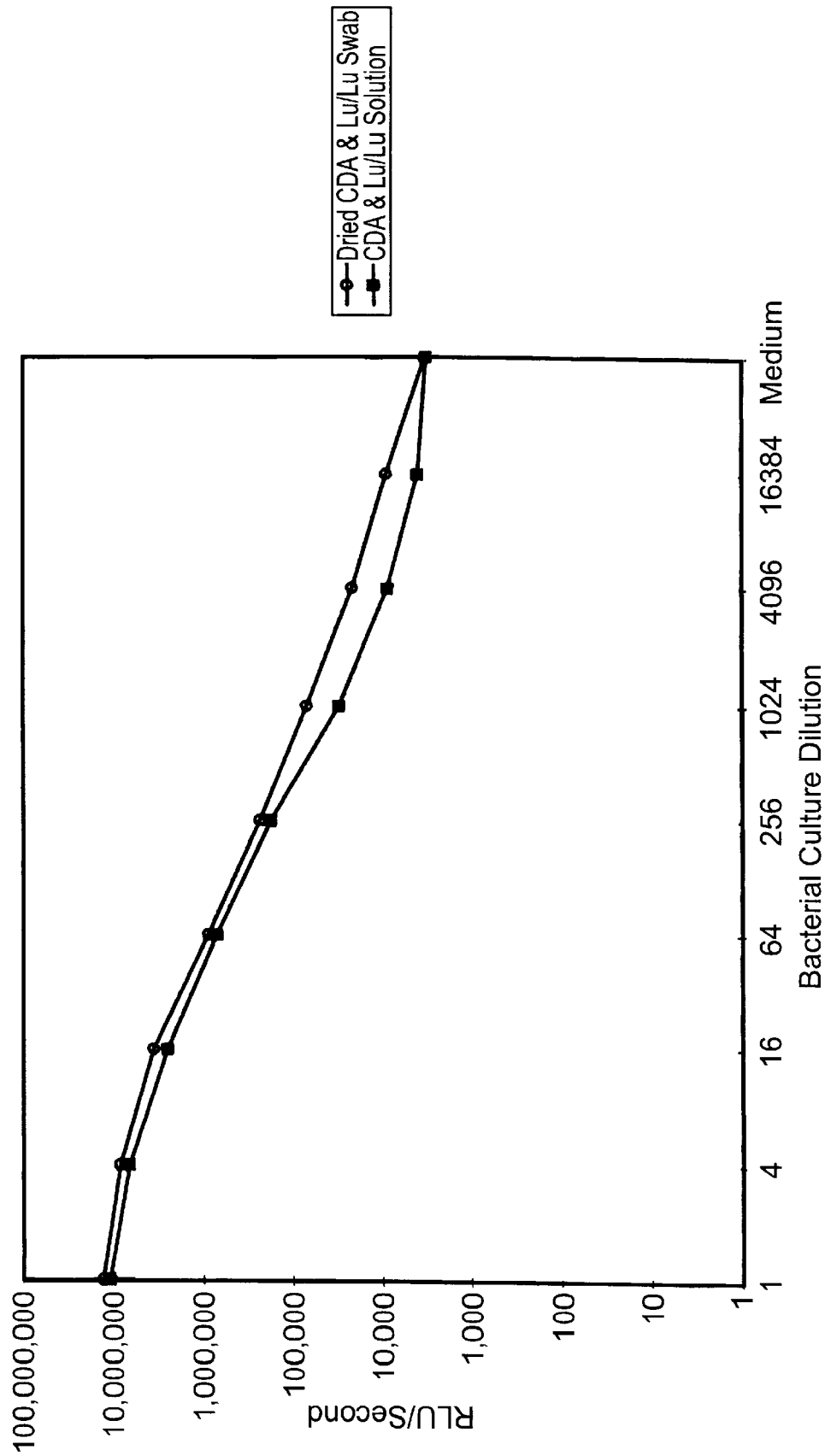
FIG. 5 depicts measurement of bacterial culture dilutions using dried CDA tube and dried luciferase/luciferin swab compared with reagents in solution.

Results obtained with dried CDA lined tubes and dried luciferase/luciferin coated swabs were compared with prior art reagent solutions for measuring different bacterial sample concentrations. The procedures of example 2 were followed except 1:4 dilutions of a bacterial culture sample were tested along with a nutrient broth background control. The samples were measured once at 3 minutes after the dried or liquid luciferase/luciferin reagent was added to the extracted sample. The results are shown in FIG. 5.

The dried CDA and luciferase/luciferin swab method had comparable sensitivity to the reagents in solution method when measuring bacterial ATP at the higher bacterial concentrations. The dried CDA and luciferase/luciferin swab method had comparable sensitivity to the reagents in solution method when measuring bacterial ATP at the lower bacterial concentrations.

Example 4

A stock 0.1% solution of CDA was prepared in distilled water. Two-fold dilutions of the 0.1% stock solution were made in distilled water to give concentrations of 0.05, 0.025, 0.0125, 0.00625, 0.00312, 0.00156 and 0.00078%. ATP extraction was tested by adding 100 μl of different bacterial cultures in nutrient broth to 100 μl of each CDA dilution, incubating the bacteria with CDA for 30–60 seconds, then adding 100 μl of luciferase/luciferin reagent and measuring RLU. The microorganisms tested included a variety of Gram-negative and Gram-positive bacteria. It was determined that the optimal CDA concentration is between 0.05% (1:2) and 0.025% (1:4). Higher and lower concentrations are less effective.

Example 5

200 μl aliquots of an *E. coli* culture were placed in polystyrene and polypropylene tubes. Next, either 2 or 3 drops of a CDA solution were added and mixed with the culture. Then, 20 μl of luciferase/luciferin reagent was added and RLU were measured every 30 seconds for 120 seconds. The results indicated that higher RLU values were obtained with polypropylene tubes. The results also confirmed that the optimal conditions were obtained with 2–3 drops of 0.05% to 0.025% CDA and a 30–60 second extraction time.

Example 6

Dried CDA tubes were prepared by adding 12.5, 25, 50, 100, and 200 μl of 0.1% CDA to each of three types of tubes: conical bottom polypropylene, conical bottom polystyrene, and round bottom polystyrene. The CDA was allowed to dry at room temperature for 72 hours. 200 μl of an *E. coli* culture was added to each tube and 20 μl of luciferase/luciferin reagent was added after an extraction time of 0, 30, 60, or 90 seconds. RLU were measured every 30 seconds for 120 seconds.

Better results were obtained for 12.5–25 μl of 0.1% CDA per tube. A 30–60 second extraction time provided optimal extraction time. Larger amounts of dried CDA resulted in less stable light output over the 120 second period.

Example 7

Dried CDA tubes were prepared by adding 12.5 and 25 μl of 0.1% CDA to each of three types of tubes: conical bottom polypropylene, conical bottom polystyrene, and round bottom polystyrene. The CDA was allowed to dry at room temperature for 72 hours. 200 μl of an *E. coli* culture was added to each tube and 20 μl of luciferase/luciferin reagent was added after an extraction time of 0, 30, or 60, seconds. RLU were measured every 30 seconds for 120 seconds.

Best results were obtained with 12.5 μl of 0.1% CDA in conical bottom polypropylene tubes and a 30–60 second extraction time. Less desirable results were obtained with 25 μl.

Example 8

The test materials used in this example included conical polypropylene tubes containing dry CDA (12.5μof 0.1% CDA), round bottom polystyrene counting tubes containing dried luciferase/luciferin counting reagent and regular untreated swabs as the sampling device. 20 μl of sample was dropped in a petri dish. A sterile swab was dipped into saline to wet it, and the entire surface of the petri dish was swabbed to pick up the sample and simulate swabbing an environmental surface to be tested. The swab was placed in a CDA tube and twisted into the bottom of the tube for one minute to extract ATP in the sample. The swab was then placed in a counting tube and twisted into the bottom of the tube for one minute before placing the tube with swab in the luminometer and counting for 5 seconds. Samples were also tested by dipping the dry untreated swab into the sample and then using extraction and counting tubes as described above.

Figure 6:
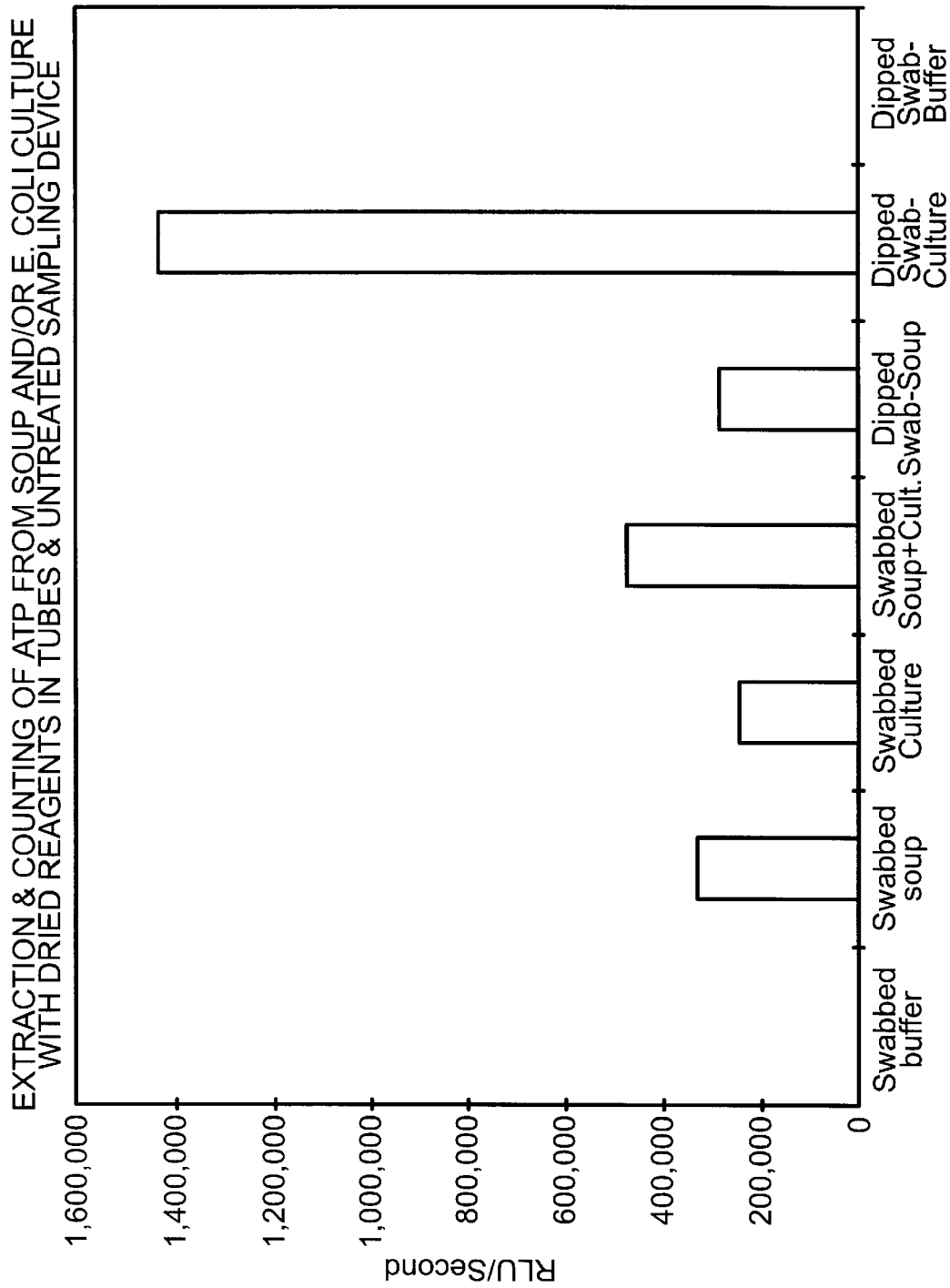
FIG. 6 depicts extraction and counting of ATP from soup and/or E. coli culture with dried reagents in tubes & untreated sampling device.

The samples tested consisted of Hepes buffer, pH 7.8, which was the negative control; soup diluted in water as a free ATP sample; and an *E. coli* culture for a bacterial sample. Soup and *E. coli* were tested together (20 μl each) to show the additive effect of the free and extracted ATP. The results are shown in FIG. 6.

Low background counts observed with the HEPES buffer sample show specificity for ATP detected with the soup and *E. coli* culture samples. The ability to quantify ATP from soup, bacterial culture, and combinations thereof, shows utility of the invention for detecting dead biomass (soup) and microorganisms (*E. coli* culture.) As expected, higher ATP was detected with the larger sample size obtained when the swab was dipped in the *E. coli* culture (approximately 125 μl sample size) compared to the 20 μl swabbed sample size.

Example 9

A 20 μl sample of HEPES buffer, soup, *E. coli* culture, or ATP solution was swabbed using a plain, sterile, untreated swab which was pre-wetted with saline. The swab was then inserted into a polypropylene tube containing dried CDA. The swab was rotated to dissolve CDA in the swab'tip and then incubated for 30–60 seconds. The swab was then inserted into a polypropylene counting tube containing dried luciferase/luciferin and rotated to dissolve the luciferase/luciferin in the tip of the swab and then incubated for 30–60 seconds. Light output (RLU/second) was measured for 5 seconds after placing the counting tube with the sampling device into luminometer. Samples were also tested in the same manner except the dried CDA extraction reagent step was not performed.

| Sample tested | Incubated with dry CDA tube | Incubated with dry luciferase/luciferin tube | RLU/second |
|---|---|---|---|
| Buffer | Yes | Yes | 742 |
| Soup (non-microbial biomass) | Yes | Yes | 436,767 |
| Soup (non-microbial biomass) | No | Yes | 406,114 |
| E. coli culture | Yes | Yes | 762,470 |
| E. coli culture | No | Yes | 10,981 |
| ATP Solution | Yes | Yes | 186,877 |
| ATP Solution | No | Yes | 179,983 |

Low background results with the buffer sample show specificity for ATP detected with soup, E. coli culture and free ATP in solution. Results with the non-microbial biomass soup sample show most of the ATP (93%) can be detected without the CDA extraction reagent step, and additional ATP presumably from beef or vegetable somatic cells in the soup can be detected using the CDA extraction reagent step. Conversely, results with the E. coli culture show that the CDA extraction reagent step is required (as expected) to detect most of the ATP (98.7%). Results with the ATP solution sample showed that the CDA extraction reagent step is not required (as expected) to detect most (96.3%) of the free ATP in solution.

It will be apparent to those skilled in the art that various modifications and variations can be made in the compositions and methods of the present invention without departing from the spirit or scope of the invention. Thus, it is intended that the present invention cover the modifications and variations of this invention provided they come within the scope of the appended claims and their equivalents.

What is claimed is:

1. A counting tube/sampling device combination comprising a counting tube having dried extraction reagent therein and a resealable cap, and a sampling device having a handle and an absorbent tip containing immobilized luciferase/luciferin reagent; wherein the handle of the sampling device is attached to the cap.

2. The combination of claim 1 wherein the tube is transparent to the lightwaves produced from the reaction of ATP and luciferase.

3. The combination of claim 2 wherein the tube is polystyrene or polypropylene.

4. The combination of claim 1 wherein the counting tube lined with dried extraction reagent is prepared by adding an extraction reagent solution to a tube wherein said extraction reagent solution comprises extraction reagent and a solvent, removing the solvent by evaporation in a refrigerator at 4° C., freeze drying, or lyophilizing.

5. The combination of claim 4, wherein the extraction reagent is chlorhexidine diacetate.

6. A counting tube/sampling device combination comprising a counting tube having dried extraction reagent therein and a resealable cap, and a sampling device having a handle and an absorbent tip containing immobilized luciferase/luciferin reagent; wherein the handle of the sample device is moveably attached to the cap.

7. The combination of claim 6 wherein the tube is transparent to the lightwaves produced from the reaction of ATP and luciferase.

8. The combination of claim 7 wherein the tube is polystyrene or polypropylene.

9. The combination of claim 6 wherein the counting tube lined with dried extraction reagent is prepared by adding an extraction reagent solution to a tube wherein said extraction reagent solution comprises extraction reagent and a solvent, removing the solvent by evaporation in a refrigertor at 4° C., freeze drying, or lyophilizing.

10. The combination of claim 9, wherein the extraction reagent is chlorhexidine diacetate.

* * * * *